(12) United States Patent
Shyi

(10) Patent No.: US 6,995,988 B2
(45) Date of Patent: Feb. 7, 2006

(54) FORWARD POWER CONVERTER WITH SELF-EXCITED SYNCHRONOUS RECTIFYING CIRCUIT

(75) Inventor: Gary Shyi, Yungho (TW)

(73) Assignee: Li Shin International Enterprise Corporation, Ta-Yuan Hsiang (TW)

( * ) Notice: Subject to any disclaimer, the term of this patent is extended or adjusted under 35 U.S.C. 154(b) by 63 days.

(21) Appl. No.: 10/829,969

(22) Filed: Apr. 23, 2004

(65) Prior Publication Data

US 2004/0196673 A1     Oct. 7, 2004

(51) Int. Cl.
*H02M 3/335* (2006.01)

(52) U.S. Cl. .............................. 363/21.06; 363/21.14; 363/127

(58) Field of Classification Search ............. 363/21.04, 363/21.06, 21.08, 21.09, 21.1, 21.14, 82, 363/89, 125, 127

See application file for complete search history.

(56) References Cited

U.S. PATENT DOCUMENTS

| 5,343,383 A | * | 8/1994 | Shinada et al. ............. 363/127 |
| 5,663,877 A | * | 9/1997 | Dittli et al. .................. 363/127 |
| 6,452,818 B1 | * | 9/2002 | Simopoulos ............. 363/21.06 |

* cited by examiner

Primary Examiner—Jessica Han
(74) Attorney, Agent, or Firm—Troxell Law Office, PLLC

(57) ABSTRACT

A forward power converter with a self-excited synchronous rectifying circuit makes use of the self-excitation function of a transformer to generate electric energy at a secondary side winding coil of the transformer, hence controlling an n-channel FET to accomplish synchronous rectification. In the synchronous rectifying circuit, the drain of the n-channel FET is connected to an end of the secondary side of a first transformer, the source of the n-channel FET is connected to a positive end of a flywheel diode, the negative end of the flywheel diode is connected to the other end of the secondary side of the first transformer, a control end of the n-channel FET is connected to an end of an induction coil via a resistor and a capacitor, and the other end of the induction coil is connected to the source of the n-channel FET.

4 Claims, 6 Drawing Sheets

FORWARD POWER CONVERTER WITH SELF-EXCITED SYNCHRONOUS RECTIFYING CIRCUIT

FIELD OF THE INVENTION

The present invention relates to a forward power converter with a self-excited synchronous rectifying circuit and, more particularly, to a forward power converter making use of the self-excitation function of a transformer to generate electric energy at a secondary side winding coil of the transformer through induction, hence controlling an n-channel FET to accomplish synchronous rectification.

BACKGROUND OF THE INVENTION

Switching power supplies (SPS) have been widely used in electronic products like information products and electric appliances. Due to the requirements for energy conservation and compactness of electronic products, how to enhance the working efficiency and power density of the SPS becomes the most important goal in this industry.

For an existent DC power supply like an AC to DC switching power supply, in order to shrink the size of a transformer, high-frequency pulse width modulation (PWM) is exploited to control the DC output voltage. FIG. 1 shows a conventional forward power converter circuit comprising a power switch Q1, a transformer T1, diodes D1, D2 and D3, an output inductor L and an output capacitor C. Its working principle is described as follows. When a PWM controller U1 turns the power switch Q1 on, an input voltage V1 provides power to a primary side winding coil N1 of the transformer T1. A current gradually builds on the winding coil to store energy therein. At the same time, a voltage having the same polarity with the primary side winding coil N1 will be induced at a secondary winding coil N2 of the transformer T1. The energy is thus forward-transferred to the secondary side winding coil N2, through the diode D1 and the output inductor L, and then to the load. At this time, the diode D2 is reverse biased, while the diode D1 is forward biased.

When the power switch Q1 is off, the polarity of the winding coil on the transformer T1 will reverse to let the diode D1 be reverse biased and thus off. The diode D2 will be on. The diode D2 is called a flywheel diode. At this time, the energy to the load is provided by the energy stored in the output inductor L and the output capacitor C via the diode D2. The output inductor L is an energy storage component.

Reference is again made to FIG. 1. The function of the transformer T1 is to isolate the primary side circuit and the secondary side circuit. Moreover, the required output voltage of the load can be obtained through the turn ratio of winding coils.

Reference is made to both FIGS. 1 and 2. When the diode D1 is on, a reverse conduction voltage Vrrm can be measured at two ends of the diode D1, and a conduction current Ic can be simultaneously measured. As shown in FIG. 2, the time from t0 to t1 is the switching time for conduction of the diodes D1 and D2. At this time, the conduction current Ic of the diode D1 will rise gradually, and the reverse conduction voltage Vrrm remains at the high level. Therefore, the converter will have a large switching loss during the switching period of the diodes D1 and D2.

SUMMARY OF THE INVENTION

Accordingly, one object of the present invention is to provide a forward power converter with a self-excited synchronous rectifying circuit, in which a primary side winding coil replaces the output inductor L of the conventional forward power converter and an n-channel FET replaces the forward diode D1. Through the self-excitation function of a transformer, electric energy is generated at the secondary side winding coil of the transformer and the n-channel FET is controlled to accomplish synchronous rectification for power supply forward transformation.

A forward power converter with a self-excited synchronous rectifying circuit of the present invention makes use of a PWM controller to drive the switching of an electronic power switch for sending an input power to a load via a first transformer, a synchronous rectifying circuit and an energy storage. In the synchronous rectifying circuit, a drain of an n-channel FET is connected to an end of the secondary side of a first transformer, a source of the n-channel FET is connected to a positive end of a flywheel diode, a negative end of the flywheel diode is connected to the other end of the secondary side of the first transformer, a control end of the n-channel FET is connected to an end of an induction coil via a resistor and a capacitor, and the other end of the induction coil is connected to the source of the n-channel FET.

The above energy storage at least comprises a primary side winding coil of a second transformer and an energy-storing capacitor. The induction coil is the secondary side winding coil of the second transformer. When forward providing energy, the primary side winding coil of the second transformer builds energy and makes use of the self-excitation of the second transformer to induce electric energy at the secondary side winding coil of the second transformer and send the energy to the control end of the n-channel FET, hence driving the n-channel FET to be on.

When there is no input power, the first transformer provides no power. At this time, the primary side winding coil of the second transformer will change its polarity and send stored energy to the load via the flywheel diode so that the load can still work without cutting off the power. The secondary side winding coil of the second transformer will simultaneously change its polarity to drive the n-channel FET to be off.

Moreover, when providing power with no load, the induced voltage of the secondary side winding coil will be smaller than the threshold drive voltage of the n-channel FET so that the n-channel FET will be off.

A forward power converter with a self-excited synchronous rectifying circuit of the present invention can make use of induced electric energy of the secondary side winding coil to provide a backup power supply for the PWM controller. When providing power with no load, a stable working power can still be provided for the PWM controller. The PWM controller will also automatically drop the frequency when no load is present, hence reducing the loss of the converter.

A forward power converter with a self-excited synchronous rectifying circuit of the present invention replaces a conventional diode with an n-channel FET and makes use of an induction coil to induce electric energy for driving the n-channel FET to be on when forward providing power, thereby reducing the power loss of circuit and enhancing the working efficiency and power density. Moreover, the whole power loss will be very small when no load is present, hence conforming to the regulation that the input power be smaller than 1W.

BRIEF DESCRIPTION OF THE DRAWINGS

The various objects and advantages of the present invention will be more readily understood from the following detailed description when read in conjunction with the appended drawing, in which.

DETAILED DESCRIPTION OF THE PREFERRED EMBODIMENTS

Figure 1:
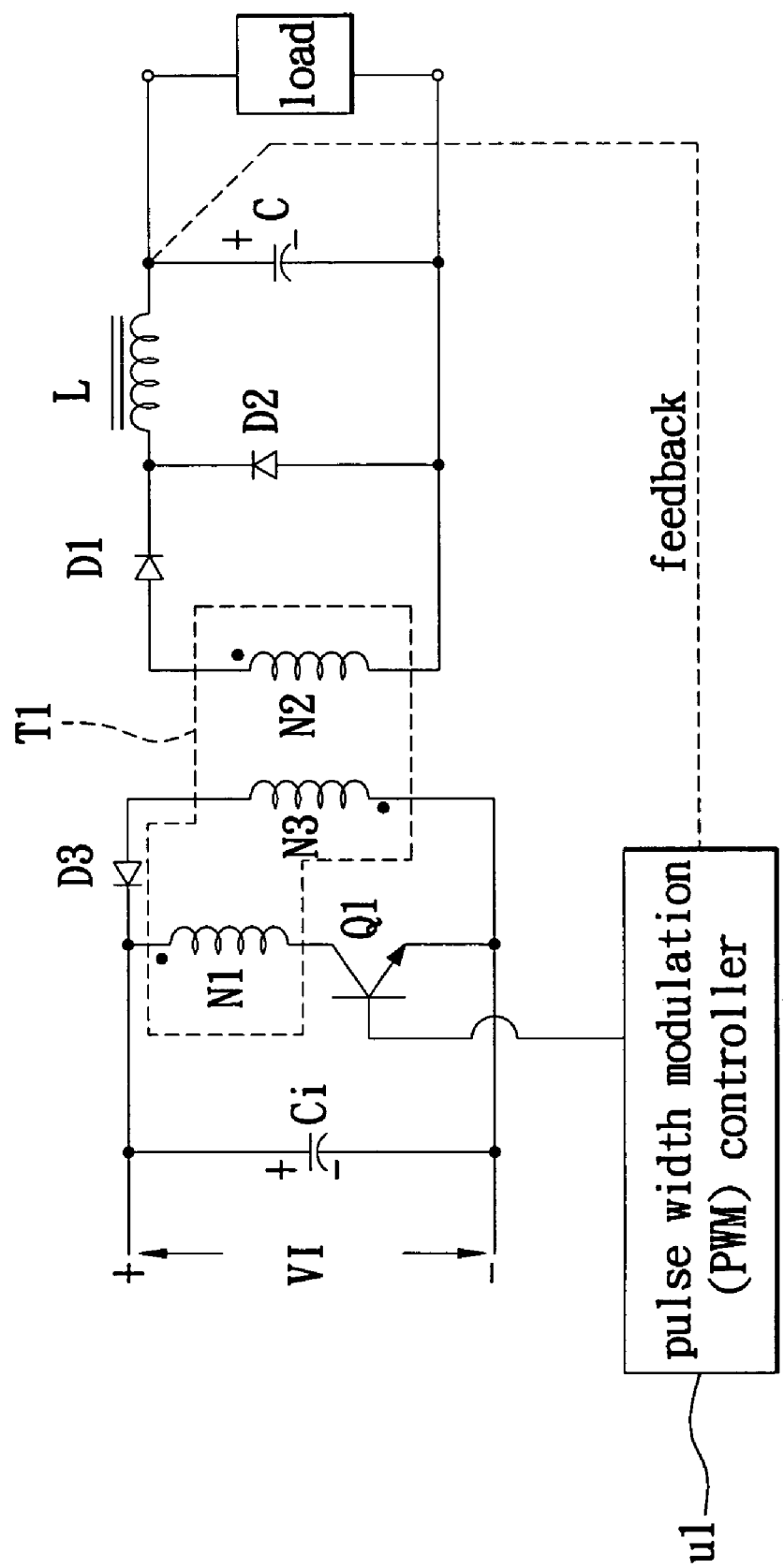
FIG. 1 is a circuit diagram of a conventional forward power converter.
Figure 2:
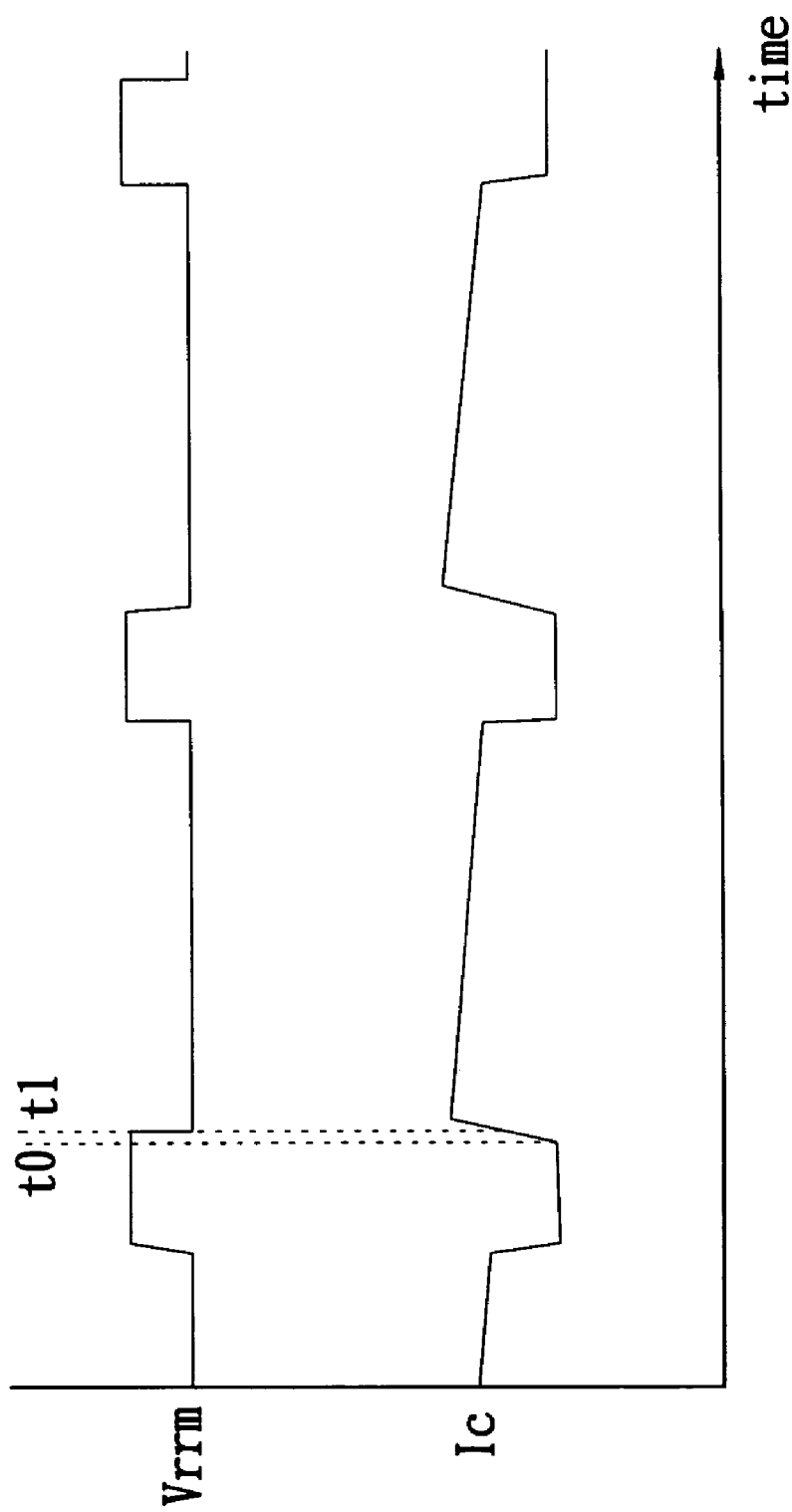
FIG. 2 is a waveform diagram of a reverse conduction voltage and a conduction current of a conventional forward power converter.
Figure 3:
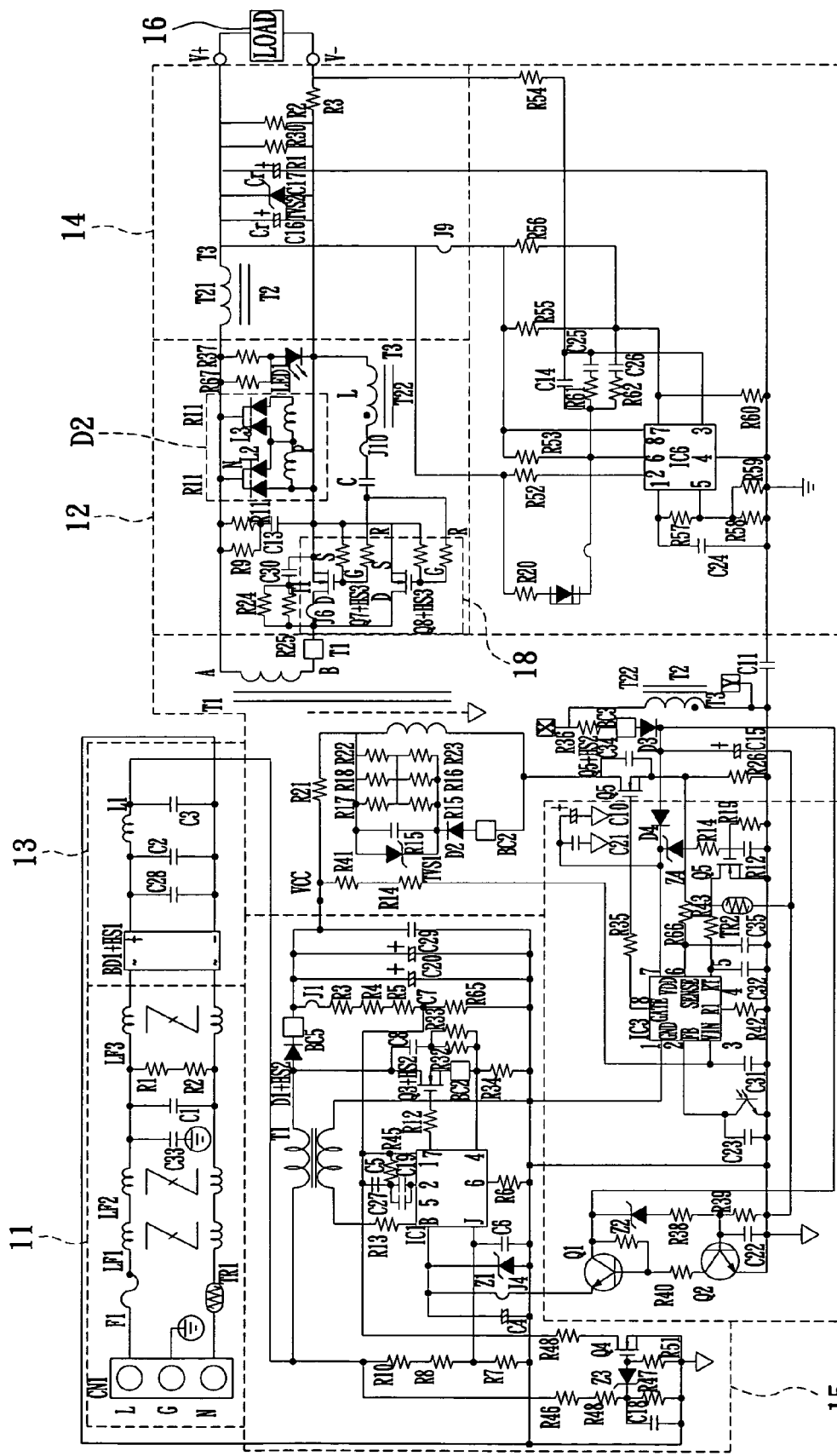
FIG. 3 is a circuit diagram of a forward power converter with a self-excited synchronous rectifying circuit of the present invention.

As shown in FIG. 3, a forward power converter with a self-excited synchronous rectifying circuit makes use of a PWM controller 10 to drive the switching of an electronic power switch Q5 for sending an input power Vcc to a load 16 via a first transformer T1, a synchronous rectifying circuit 12 and an energy storage 14. In the synchronous rectifying circuit 12, a drain D of an n-channel FET 18 is connected to an end B of the secondary side of a first transformer T1, a source S of the n-channel FET 18 is connected to a positive end (P) of a flywheel diode D2, a negative end (N) of the flywheel diode D2 is connected to the other end A of the secondary side of the first transformer T1, a control end G of the n-channel FET 18 is connected to an end of an induction coil L via a resistor R and a capacitor C, and the other end of the induction coil L is connected to the source S of the n-channel FET 18.

Reference is again made to FIG. 3. An electromagnetic interference protection circuit 11 is used for protection of the power source and prevention of electromagnetic interference. An AC power is rectified by a rectification/filter circuit 13 to become a DC power with a low AC ripple. The DC power is then improved for the power factor of the whole power system by a power factor correction circuit 15 to meet the regulation requirements. After the DC power is improved for the power factor by the power factor correction circuit 15, the required input power VCC of the present invention is acquired.

As shown in FIG. 3, the energy storage 14 comprises a primary side winding coil T21 of a second transformer T2, at least an energy-storing capacitor Cr and at least a resistor R1. The induction coil L is a secondary side winding coil T22 of the second transformer T2.

When the PWM controller 10 drives the electronic power switch Q5 to be on, the input power VCC will be sent to the secondary side via the primary side of the first transformer T1, and then to the load 16 via the primary side winding coil T21 of the second transformer T2. At the same time, the primary side winding coil T21 of the second transformer T2 stores energy, and the secondary side winding coil T22 induces electric energy to drive the n-channel FET 18 to be on, thereby forming a power supply loop to provide power for the load 16.

When the PWM controller 10 drives the electronic power switch Q5 to be off, there will be no power provided for the primary side of the first transformer T1 by the input power VCC. The secondary side of the first transformer T1 thus can't provide power for the load 16. At this time, the primary side winding coil T21 of the second transformer T2 will change its polarity and send the stored energy to the load 16 via the flywheel diode D2 so that the load 16 can still work. The secondary side winding coil T22 of the second transformer T2 simultaneously changes its polarity to drive the n-channel FET 18 to be off.

When the PWM controller 10 drives the electronic power switch Q5 to be on or off, the secondary side winding coil T22 of the second transformer T2 is connected to a backup power source terminal of the PWM controller 10 to provide a backup power for the PWM controller 10.

Figure 4:
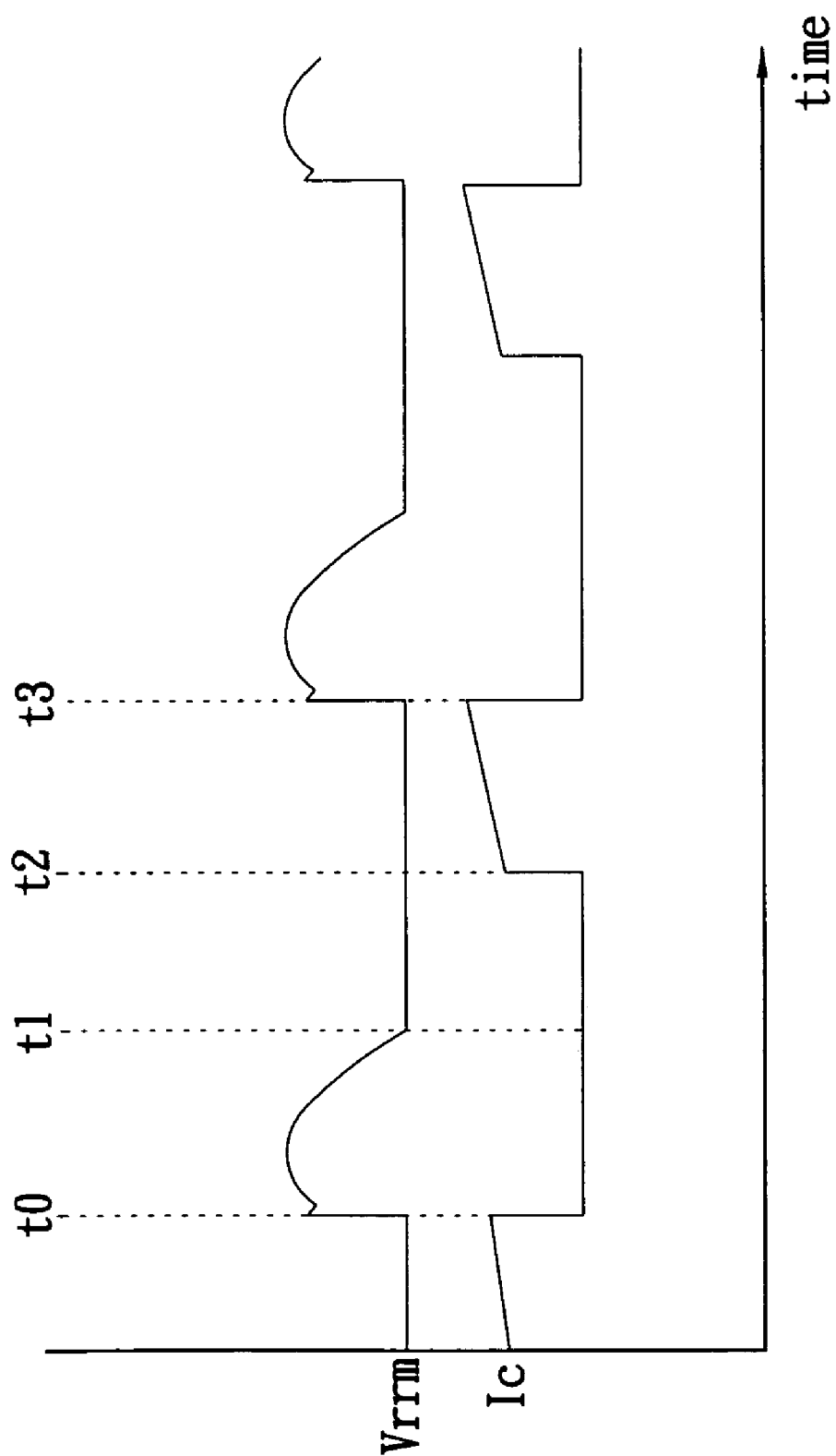
FIG. 4 is a waveform diagram of a reverse conduction voltage and a conduction current of an n-channel FET of the present invention.

Reference is made to FIGS. 3 and 4. At time t0 to t1, the n-channel FET 18 is off and there is no conduction current Ic. Moreover, the reverse conduction voltage Vrrm between the drain D and the source S of the n-channel FET 18 is the voltage generated at the secondary side when the first transformer T1 discharges energy. This voltage is a descending voltage. At this time, because there is no conduction current Ic, there is no power loss.

At time t2 to t3, the n-channel FET 18 is on to produce a conduction current Ic. The reverse conduction voltage Vrrm between the drain D and the source S of the n-channel FET 18 is near a zero potential. At this time, because the reverse conduction voltage Vrrm is near a zero potential, there is also no power loss.

From the above illustrations, the power loss is very small when the n-channel FET 18 used in the present invention is switched between the on and off states. Therefore, the power supply efficiency can be enhanced, and the working temperature can be lowered.

Figure 5:
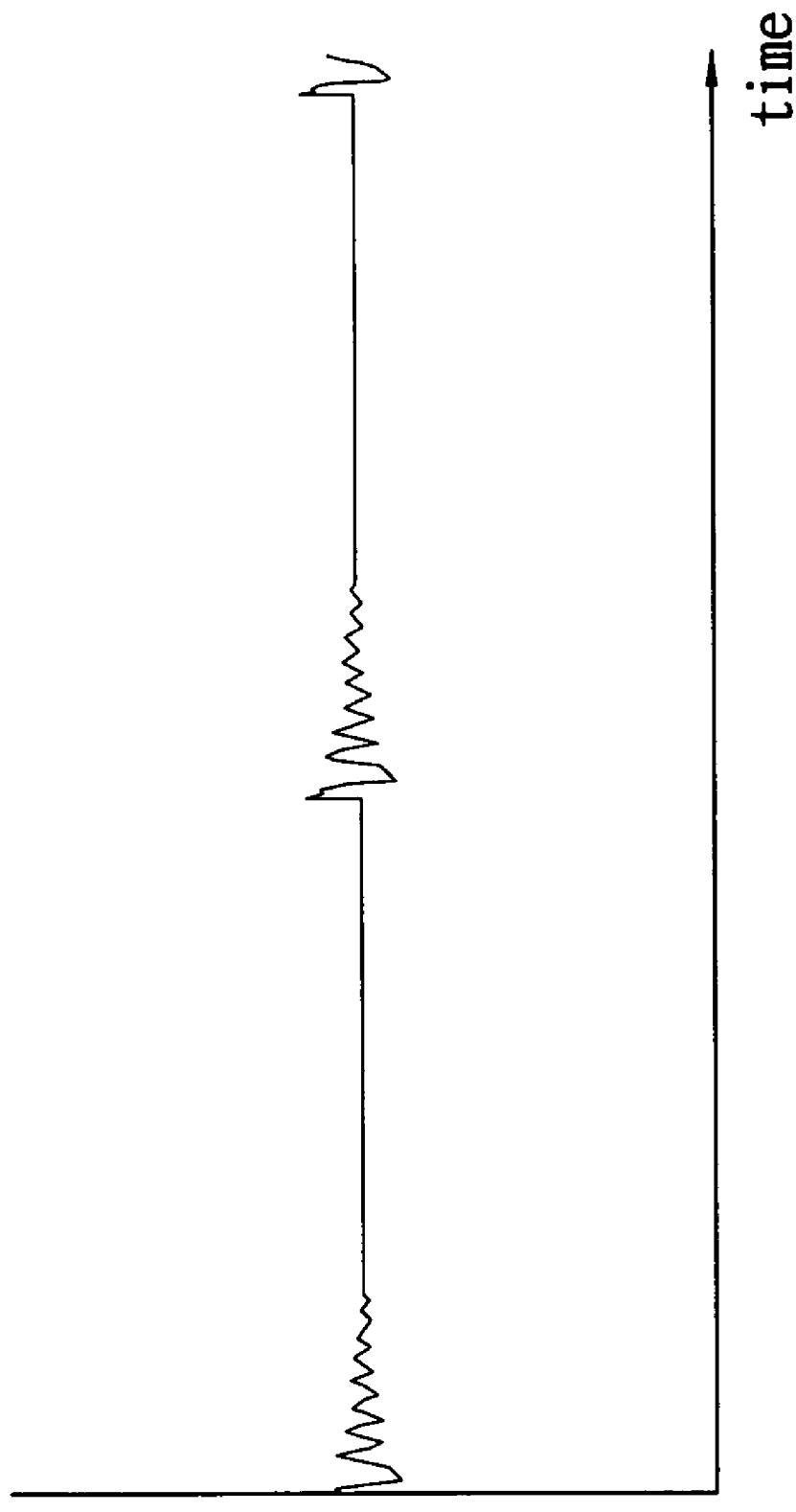
FIG. 5 is a waveform diagram of a drive signal of an n-channel FET of the present invention with no load.

Reference is made to FIGS. 3 and 5. When there is no load, the induced voltage at the secondary side winding coil T22 of the second transformer T2 will be smaller than the threshold drive voltage of the n-channel FET 18 so that the n-channel FET 18 will be off. The induced voltage at the secondary side winding coil T22 of the second transformer T2 is a drive signal S1 of the n-channel FET 18 when there is no load.

Figure 6:
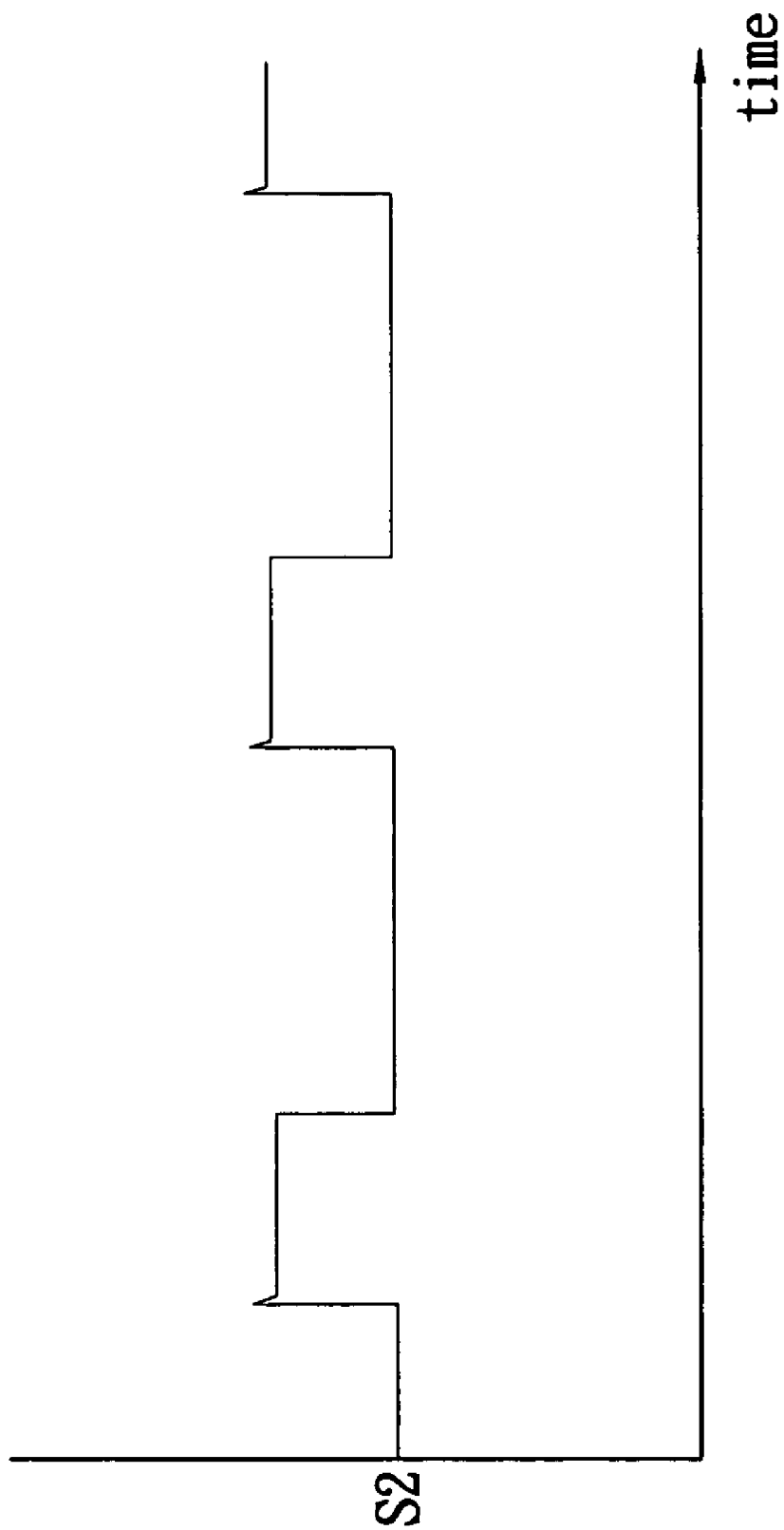
FIG. 6 is a waveform diagram of a drive signal of an n-channel FET of the present invention with a full load.

Reference is made to FIGS. 3 and 6. When at full load, the induced voltage at the secondary side winding coil T22 of the second transformer T2 will be larger than the threshold drive voltage of the n-channel FET 18 so that the n-channel FET 18 will be on. The induced voltage at the secondary side winding coil T22 of the second transformer T2 is a drive signal S2 of the n-channel FET 18 when at full load.

As shown in FIG. 3, the present invention can make use of the induced voltage at the secondary side winding coil T22 of the second transformer T2 as a backup power source to provide power for the PWM controller 10. When providing power with no load, a stable working power can still be provided for the PWM controller 10. The PWM controller 10 can further reduce frequency with no load to reduce the loss of converter.

When the forward power converter with a self-excited synchronous rectifying circuit provides power in the forward direction, the primary side winding coil T21 of the second transformer T2 builds energy. Through the self-excitation function of the second transformer T2, electric energy will be induced at the secondary side winding coil T22 of the second transformer T2 and sent to the control end G of the n-channel FET 18 for driving the n-channel FET 18 to be on.

When providing power with no load, the induced voltage at the secondary side winding coil T22 of the second transformer T2 will be smaller than the threshold drive voltage of the n-channel FET 18 so that the n-channel FET 18 will be off.

The forward power converter with a self-excited synchronous rectifying circuit of the present invention can make use of the induced voltage at the secondary side winding coil T22 of the second transformer T2 as a backup power source to provide power for the PWM controller 10. When providing power with no load, a stable working power can still be provided for the PWM controller 10. The PWM controller 10 can further reduce frequency with no load to reduce the loss of converter.

To sum up, a forward power converter with a self-excited synchronous rectifying circuit of the present invention replaces a conventional diode with an n-channel FET and makes use of an induction coil to induce electric energy for driving the n-channel FET to be on when forward providing power, thereby reducing the power loss of circuit and enhancing the working efficiency and power density. Moreover, the whole power loss will be very small with no load, hence conforming to the regulation that the input power be smaller than 1W.

Although the present invention has been described with reference to the preferred embodiment thereof, it will be understood that the invention is not limited to the details thereof. Various substitutions and modifications have been suggested in the foregoing description, and other will occur to those of ordinary skill in the art. Therefore, all such substitutions and modifications are intended to be embraced within the scope of the invention as defined in the appended claims.

I claim:

1. A forward power converter with a self-excited synchronous rectifying circuit making use of a PWM controller to drive switching of an electronic power switch for sending an input power to a load via a first transformer, a synchronous rectifying circuit and an energy storage, in said synchronous rectifying circuit, a drain of an n-channel FET being connected to an end of the secondary side of a first transformer, a source of said n-channel FET being connected to a positive end of a flywheel diode, a negative end of said flywheel diode being connected to another end of the secondary side of said first transformer, a control end of said n-channel FET being connected to an end of an induction coil via a resistor and a capacitor, and another end of said induction coil being connected to said source of said n-channel FET.

2. The forward power converter with a self-excited synchronous rectifying circuit as claimed in claim 1, wherein said energy storage at least comprises a primary side winding coil of a second transformer and a capacitor.

3. The forward power converter with a self-excited synchronous rectifying circuit as claimed in claim 1, wherein said induction coil is a secondary side winding coil of a second transformer.

4. The forward power converter with a self-excited synchronous rectifying circuit as claimed in claim 1, wherein said PWM controller is connected to a secondary side winding coil of a second transformer for providing a backup power supply.

\* \* \* \* \*